United States Patent [19]

Cotter et al.

[11] Patent Number: 4,973,122
[45] Date of Patent: Nov. 27, 1990

[54] OPTICAL NONLINEAR CROSS-COUPLED INTERFEROMETER AND METHOD UTILIZING SAME

[75] Inventors: David Cotter, Woodbridge; Nicholas J. Doran, Cambridge; Keith J. Blow; David C. Wood, both of Woodbridge, all of England

[73] Assignee: British Telecommunications public limited company, United Kingdom

[21] Appl. No.: 382,634
[22] PCT Filed: Dec. 9, 1988
[86] PCT No.: PCT/GB88/01086
§ 371 Date: Aug. 2, 1989
§ 102(e) Date: Aug. 2, 1989
[87] PCT Pub. No.: WO89/05472
PCT Pub. Date: Jun. 15, 1989

[30] Foreign Application Priority Data
Dec. 10, 1987 [GB] United Kingdom ............... 8728854

[51] Int. Cl.⁵ .................. G02B 6/26; G01B 9/02; H01J 5/16; H03K 17/80
[52] U.S. Cl. ................. 350/96.15; 350/96.12; 350/96.29; 350/96.30; 350/320; 356/350; 250/227.11; 250/227.19; 307/407; 307/409
[58] Field of Search ............ 350/96.10, 96.15, 96.16, 350/96.29, 96.30, 96.12, 96.13, 320; 307/425, 426, 427, 428, 429, 430, 407, 409; 356/350; 372/6; 250/227.11, 227.19

[56] References Cited

U.S. PATENT DOCUMENTS

| 3,558,213 | 1/1971 | Marcatili | 350/96.11 X |
|---|---|---|---|
| 3,589,794 | 6/1971 | Marcatili | 350/96.11 X |
| 4,440,498 | 4/1984 | Sheem | 356/350 |
| 4,456,377 | 6/1984 | Shaw et al. | 356/350 |
| 4,558,921 | 12/1985 | Hasegawa et al. | 350/96.29 |
| 4,632,518 | 12/1986 | Jensen | 350/354 |
| 4,633,524 | 12/1986 | Hasegawa | 455/612 |
| 4,635,263 | 1/1987 | Mollenauer | 372/6 X |
| 4,637,722 | 1/1987 | Kim | 356/350 |
| 4,687,330 | 8/1987 | LeFevre | 356/350 |
| 4,699,452 | 10/1987 | Mollenauer et al. | 350/96.16 |
| 4,700,339 | 10/1987 | Gordon et al. | 370/3 |
| 4,707,136 | 11/1987 | Kim | 356/350 |
| 4,741,587 | 5/1988 | Jewell et al. | 350/96.15 |
| 4,749,248 | 6/1988 | Aberson, Jr. et al. | 350/96.15 X |
| 4,805,975 | 2/1989 | Utaka et al. | 350/96.15 X |
| 4,839,898 | 6/1989 | Payne et al. | 372/6 |
| 4,853,534 | 8/1989 | Dakin | 250/227.17 X |
| 4,881,788 | 11/1989 | Doran | 350/96.15 |
| 4,885,462 | 12/1989 | Dakin | 250/227.19 X |
| 4,904,050 | 2/1990 | Dunn et al. | 350/96.29 |

FOREIGN PATENT DOCUMENTS

WO8601007 2/1986 PCT Int'l Appl. .......... 350/96.15 X

OTHER PUBLICATIONS

Mollenauer et al., "The Soliton Laser", Optics Letters, vol. 9, No. 1, pp. 13–14, Jan. 1984.
Otsuka, "Nonlinear Antiresonant Ring Interferometer", Optics Letters, vol. 8, No. 9, pp. 471–473, 9/1983.
Frigo et al., "Optical Kerr Effect in Fiber Gyroscopes: Effects of Nonmonochromatic Sources", Optics Letters, vol. 8, No. 2, pp. 119–121, 2/1983.
Doran et al., "Solitons in Optical Communications", IEEE Journal of Quantum Electronics, vol. QE-19, No. 12, pp. 1883–1888, 12/1983.
Crosignani et al., "Optical Multistability in a Fiber-Optic Passive-Loop Resonator", Optics Communications, vol. 59, No. 4, pp. 309–312, 9/1986.

(List continued on next page.)

Primary Examiner—Brian Healy
Attorney, Agent, or Firm—Nixon & Vanderhye

[57] ABSTRACT

An optical device includes a 50-50 cross-coupler having a pair of ports optically coupled by a waveguide which includes a portion of material having a non-linear refractive index with a relaxation time such that the effect on the non-linear portion of a first pulse passing through the portion last long enough to affect the phase of a second pulse relative to the first. It finds application as a logic element, optical amplifier modulator and the like.

7 Claims, 1 Drawing Sheet

OTHER PUBLICATIONS

Eichmann et al., "Digital Optical Logic Using a Pulsed Sagnac Interferometer Switch", *Optical Engineering*, vol. 25, No. 1, pp. 91–97, 1986.

Kawaguchi et al., "Proposal for a New All-Optical Waveguide Functional Device", *Optics Letters*, vol. 10, No. 8, pp. 411–413, 8/1985.

Optics Communications, vol. 59, No. 4, 15th Sep. 1986, pp. 309–312, Elsevier Science Publishers B.V., NL; B. Crosignani et al: "Optical multistability in a fiber-optic passive-loop resonator".

Optical Engineering, vol. 25, No. 1, Jan. 1986, pp. 91–97, Society of Photo-Optical Instrumentation Engineers, US; G. Eichmann et al: "Digital optical logic using a pulsed sagnac interferometer switch".

Optics Letters, vol. 8, No. 9, Sep. 1983, pp. 471–473, Optical Society of America, US; K. Otsuka: "Nonlinear antiresonant ring interferometer".

Applied Physics B, vol. B 38, No. 1, Sep. 1985, pp. 31–36, Springer-Verlag; B. Danielzik et al: "Nanosecond optical pulse shaping in cadmium-sulfide-selenide glasses".

OPTICAL NONLINEAR CROSS-COUPLED INTERFEROMETER AND METHOD UTILIZING SAME

BACKGROUND OF THE INVENTION

1. Field of the Invention

This invention relates to an optical device, particularly but not exclusively for use as an optical amplifier, modulator or logic element.

Throughout this specification by interferometric coupled loop is meant a device having an optical cross-coupler having a first and a second pair of communication ports which splits an optical signal received at one port of given pair of ports to the two ports of the other pair of ports and an optical waveguide optically coupling the first pair of ports. In such a device, light entering one of the ports of the second pair of ports is split into two portions having relative intensities determined by the coupling ratio of the cross-coupler which portions exit respective ports of the first pair of ports to travel in opposite directions around the waveguide to re-enter the cross-coupler. The two portions are then each cross-coupled to the two ports of the second pair of ports where recombination takes place to provide two outputs. The term "optical" is intended to refer to that part of the electro-magnetic spectrum which is generally known as the visible region together with those parts of the infra-red and ultra-violet regions at each end of the visible region which are capable of being transmitted by dielectric optical waveguides such as optical fibres.

2. Related Prior Art

As is well known, a linear interferometric coupled loop with a 50:50 coupling ratio acts as a mirror in that a signal entering the cross-coupler at a port of the second pair of ports will exit entirely from that same port, none being output from the other port of the second pair. This is because the two signal portions travelling in opposite directions round the waveguide have no relative phase shift when they re-enter the coupler and so they each split in two portions on cross-coupling which destructively and constructively interfere at the second pair of ports. A paper entitled "Soliton logic elements for all-optical processing" by N. J. Doran, K. J. Blow and D. Wood Proc O-E Fibre, San Diego (1987) discloses an interferometric coupled loop which utilizes the instantaneous Kerr nonlinearity of the refractive index of silica to provide an output which is a function of the intensity of the light entering the input port by providing a coupler with a coupling ratio that is not 50:50. The two portions of the optical signal therefore have different intensities and so experience different instantaneous refractive indices throughout their passage around the loop. This gives rise to a phase shift proportional to the intensity and the distance propagated, referred to as self-phase modulation (SPM), different for the two portions. The result of the differently phase shifted signal portions arriving back at the coupler is that signals of different intensities are output from the two ports of the first pair of ports which can be used in a variety of applications including logic elements, optical amplifiers, modulators and the like.

There are several disadvantages associated with the use of this known device for pulsed signals. Because the effect responds rapidly (about 5 fs) to the varying local optical intensity the SPM will vary with the local intensity throughout the pulse. For fast, in the order of GHz, operations the pulses will not in general be square and so the variable SPM seriously degrades the characteristics of the device by producing incomplete switching and a poor on-off contrast ratio. As proposed in the above referenced paper, the efficiency can be improved in this pulse mode of operation if group-velocity dispersion effects are taken into account and the pulses are so shaped and are of sufficient power so as to propagate in or near the soliton regime. The Kerr coefficient in silica is small ($n_2 = 3.2 \times 10^{-16}$ cm$^2$W$^{-1}$) which combined with the need for significant dispersion necessary to obtain soliton propogation requires a relatively long non-linear waveguide (from 1 to 4 m) and high power densities and appropriate pulse shaping. Also, when such known devices are used for logic operations between two or more signal streams, perhaps distantly originated, they must be coherent which is a very severe practical limitation.

SUMMARY OF THE INVENTION

It is an object of the present invention to largely overcome these advantages. Accordingly there is provided an optical device comprising a coupling means having a first and a second pair of optical communication ports in which optical pulse signals received at a port of one pair are coupled substantially equally into each port of the other pair, and an optical waveguide optically coupling together the first pair of ports, the optical waveguide including a portion of a material located non-equidistantly between the first pair of ports and having a non-linear refractive index with a relaxation time such that the effect on the non-linear portion of the first counter propagating pulse to pass through the portion lasts long enough to alter the phase of the second counter propagating pulse relative to the first pulse.

Because the non-linear element is located nearer one of the ports of the first pair of ports, one pulse portion (the 'first' counter-propagating pulse) split from an input pulse to the cross-coupler will reach it before the other pulse portion (the 'second' counter-propagating pulse). As the first pulse traverses the non-linear element it alters its refractive index, which change lasts for a time after this first pulse leaves this element due to the size of its relaxation time. The second pulse then traverses the non-linear portion and will experience an average refractive index different from that experienced by the first pulse and it therefore arrives back at the cross-coupler phase shifted relative to the first pulse. As in the known soliton regime interferometric coupled loop, this relative phase shift produces a transfer characteristic that is an oscillatary function of the intensity of the input optical pulse. However, by using a material having a non-linear refractive index with a relatively long relaxation time (a so called integrating response) so that the first pulse can influence the phase of the second pulse propagating round the loop in contrast to known devices which rely on the essentially instantaneous Kerr response and self-phase modulation, efficient switching of entire pulses is achieved in the region of negligible dispersion in which soliton effects are not supported and regardless of pulse shape or spectral quality. Also, optical logic operations can be performed using pulses which are not necessarily mutually coherent as will be explained below.

BRIEF DESCRIPTION OF THE DRAWINGS

The principle of operation of the present invention and an embodiment therefore will now be described by way of example only with reference to the accompanying drawings in which -

DETAILED DESCRIPTION OF PREFERRED EMBODIMENTS OF THE INVENTION

Figure 1:
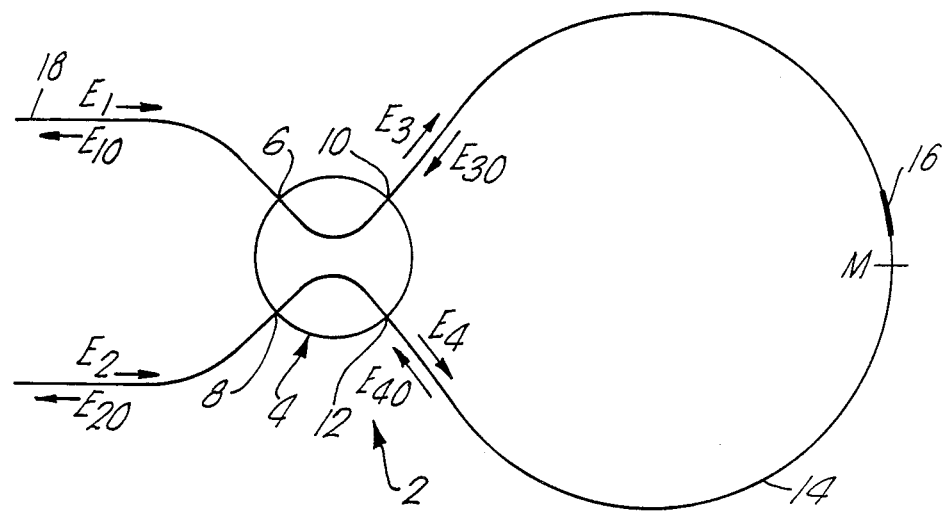
FIG. 1 is a schematic diagram of an interferometric coupled loop according to the present invention.

The principle of operation of the invention will first be analysed by reference to FIG. 1 which shows an interferometric coupled loop 2 comprising a 50:50 cross-coupler 4 having a first pair of ports 6 and 8 and a second pair of ports 10 and 12. The ports 10 and 12 are optically coupled together by an optical waveguide 14 of length L which includes an portion 16 of length 1 of a material having an integrating non-linear refractive index response located with its end nearer the waveguide midpoint M a distance x.L from the nearer port 10. All references to equations are to those of Appendix A.

The coupling equations for the interferometic coupled loop 2 are as at equations (1a) and (1b).

Assuming that the length and other characteristics of the waveguide 14 have negligible effect on the phase-velocity dispersion, counter propagating pulses (not shown) travelling round the waveguide 14 and arriving at ports 12 and 10 are related to the respective pulses leaving 10 and 12 as at equations (2a) and (2b). Using equations (1a) and (1d) and setting $E_2=0$ we obtain equations (3a) and (3b).

Assuming further that the counter-propagating pulses do not over lap in the element 16 so that coherent inteference effects are avoided, that the waveguide has negligible non-linearity outside the portion 16 and that $1 << L$, we obtain equation (4).

The values of the phase shifts for the pulses differ because the phase integral for the pulse arriving second at the portion 16 includes the effects of the first pulse on that portion 16. If parts of pulses, originating from a series of input pulses to the device having a repetition rate rate R is such that $t_E R < 1$ and that $t_T R >> 1$, then equation (4) can be written as shown in equation (5) on making the substitutions shown at (5a) and (5b).

Since the pulses are assumed not to overlap at the non-linear element 16, and it was assumed that the pulse duration is much smaller than $t_E$ it follows that the values for the phase shifts to be inserted in equation (3) are given by equation (6a) and (6b).

Finally, by combining (3b) and (6a) and (6b) and substituting for $E_3(t)$ and $E_4(t)$ from (1) we obtain equation (7) on making the substitution (7a) from which the transfer characteristic for the device is seen to take the simple form at equation (8).

A number of important conclusions follow from these results. First, the transfer characteristic is independent of the magnitude of the thermal nonlinearity so the device is immune from the effects of average-power fluctuations. This is in contrast to other configurations, such as the Mach-Zehnder, in which the slow thermal nonlinearity may dominate or even cancel the required fast nonlinearity. Second, equation (8) shows that the loop reflectivity is oscillatory with input pulse energy, and that the transmission via the port 8 should reach 100% of $E_1$ whenever the incident energy is such that equation (1) equals $(2m+1)\pi$ for integers $m \geq 0$ in which case the device transfer characteristic depends only on the total energy of the input pulse, is independent of pulse shape and does not vary as a function of time during the pulse. The reason for this can be seen from the analysis at Appendix A: whilst the phase factors are each time dependent, they differ only by the time independent factor defined by equation (7a), so in principle the whole of the input pulse can be switched with 100% efficiency—in other words, operations can be performed on entire pulses. In contrast to the known soliton device, such efficient switching is obtainable regardless of the input pulse shape or spectral quality.

The fundamental difference in principle between the device according to the present invention and known nonlinear inteferometric coupled loops is that the induced refractive-index change depends on integrals over the pulse-intensity envelope, rather than the instantaneous intensity. The nonlinear material can therefore be thought of as a short-term memory element in which pulse energy information from a first traversing pulse is retained thereby causing a second counter propagating pulse to see a different optical path length to the first and so be shifted in phase relative to the first pulse.

Yumoto et al in a paper entitles "Observation of 25 ps Optical Bistable Switching in Cd $S_x Se_{1-x}$ Doped Glass", post deadline paper ThuU 15-1, Proc. Conf Lasers and Electro-optics, Baltimore (1987) report that a bulk sample of $CdS_x Se_{1-x}$ doped glass exhibited an induced refractive index change of about $10^{-4}$ over an effective path length of about 6 mm for an effective pulse energy density of 60 $\mu J$ $cm^{-2}$. Given that it has an electronic relaxation time $t_E = 50$ ps (as measured by the applicant) and on the assumption that a doped fibre has a comparable non-linearity to the bulk sample, a non-linear element of this material which is 3 mm long and has a fibre core diameter of 2 $\mu m$ in a 100 mm waveguide (chosen for convenience of construction) is calculated to provide complete switching of optical pulses of pulse duration 5 ps at a repetition rate of 1 $GH_Z$ for incident pulse energies of about 3 pJ. The device can be manufactured by butt-jointing the short length of monomode semiconductor-doped fibre 16 into a silica optical fibre from which is fabricated the fused coupler 4 with the doped fibre in the appropriate position in a known manner.

For maximum effect of the first pulse on the second pulse, the nonlinear portion 16 should be located as close as possible to the midpoint M of the waveguide 14 without allowing the first and second pulses to overlap at any time in the portion 16. If the distance is greater than this the effect of the first pulse on the non-linearity will have decayed further by the tie the second pulse passes through so the effect on its phase will be less, for a given input pulse intensity.

It should be noted that if a longer portion 16 is used, the relative contribution of a unit additional length has an exponentially decreasing contribution to the relative phase shift of the second pulse. There is therefore expected to be an maximum effective length $1_{eff}$ of portion 16 of $n.t_E/c$ which represents, in broad terms only, an approximate practical limit on the portion length. Longer portions have increasingly less effect while introducing additional losses.

For $t_E = 50$ ps this gives $$l_{eff} = \frac{3 \times 10^8}{1.5} \times 50 \times 10^{-12} \text{ m} = 10 \text{ mm}.$$

A length of 3 mm was chosen for the illustrated embodiment of the invention. For a laser source providing 5 ps pulses at 600 nm into a monomode fibre of 2 μm core diameter the expected necessary switching pulse energy can be calculated as follows.

Yumoto et al in their above referenced paper measured $$N_E \int_{-\infty}^{\infty} |E_1(t)|^2 \, dt \simeq 10^{-4}$$

for 60 uJ/cM² incident pulse energy density.
where
 E=pulse energy; and
 A=effective pulse core area.
Substitution into equation (9) gives $$\exp(-t_D/t_E) \cdot \frac{1.10^{-4} E}{\lambda \, Fo \cdot A} = 1$$

Here $t_D=25$ ps and $t_E=50$ ps $\lambda=600$ nm, $1=3$ mm, Fo=60 μJ/cm$^{-2}$ and A=1.6×10$^{-12}$ m² which gives E=3.2 pJ.

The total loop length is set by mechanical constraints and here is conveniently 100 mm.

Just as the non-linear portion 16 should be positioned as close to the optimum position to achieve maximum cross-effects from one pulse to the other, so $t_E$ should be large relative to $t_L$ although it is limited by $t_e R < 1$. A range of values of $t_E$ is possible but the smaller the $t_E$ the less the residual effect on the second pulse. Smaller pulse durations allow the non-linear portion to be positioned nearer the midpoint and so can switch for a smaller $t_E$ for give pulse energy.

In order to determine the optimum position of the portion 16 prior to manufacture of a device, a section of the waveguide can be replaced by a variable length air path which is varied while performance of the device is monitored.

The invention is not restricted to the above described embodiment but will function with other forms of couplers and with waveguides other than those formed from optical fibres, for example planar waveguides formed from semiconductor doped glass. Also, other non-linear materials can be used as the non-linear element, for example III-V semiconductor with carrier recombination times of 1-1000 ps may be found to be useable.

The nonlinear transfer characteristic indicated by equation (8) can be used to perform various signal-processing functions, such as pulse clipping, differential gain, and self-switching. With mutually-coherent input pulses applied simultaneously at ports 1 and 2, further operations which can be performed such as optical amplification, cross-switching, and optical-logic functions however. The need for mutual coherence is however a severe limitation for practical applications but unlike the hitherto known optical devices, devices according to the present invention can in certain methods of use be used to perform all-optical logic operations at high speed using input pulses which are not mutually coherent as will now be explained by reference to FIG. 2.

Figure 2:
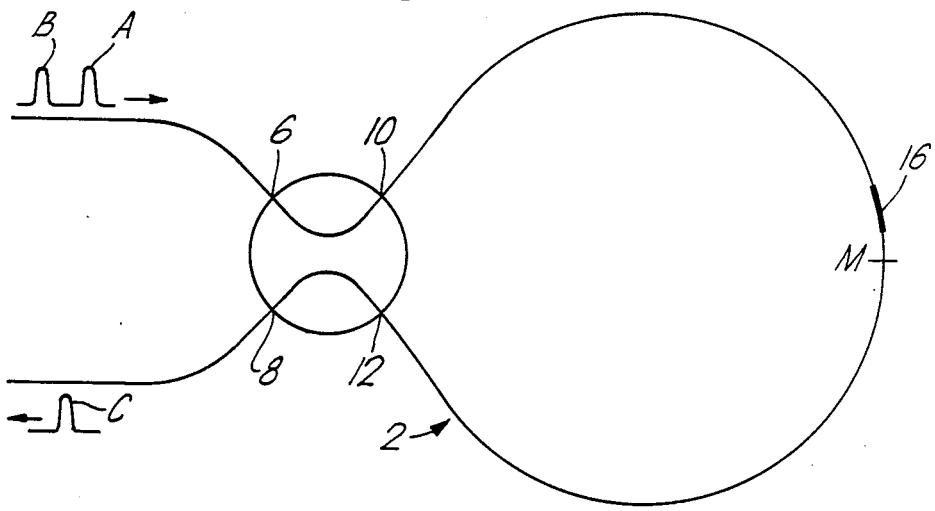
FIG. 2 is a schematic diagram of the device of FIG. 1 to show its use as an XOR gate.

In FIG. 2, two input pulses, labelled A and B, are applied in series to the coupler 4 at port 6 and the output signal, labelled C, is detected after emerging from port 2. The A and B pulses are assumed to be similar in duration, and as close together in time as possible without significant overlap. The absence of an input pulse represents a logical value 0, if present a logical value 1. Each of the pulses A and B is arranged to have the required energy to satisfy equation (9).

As can be seen by reference to equation (14) the pulses must be equal in energy, but they need not be mutually coherent. Because the A and B input pulses are non-overlapping, each pair of counter-propagating pulses corresponding to the A or B input pulse in the fibre loop interferes at the coupler in their separate pairs. The element 16 is located in a position such that the pair of pulses from port 10 both traverse the element 16 before the pair of pulses from port 12 arrives at the element 16. Following an identical analysis to that above, we find that if only one pulse is present at the input (A32 1, B=0 or A=0, B=1), an equal-energy pulse is transmitted from port 8 (C=1). If however both input pulses are present (A=B=1), then the induced phase shifts between the counter-propagating A pulses, and between the counter-propagating B pulses, are both $2\pi$ so no pulse is transmitted (C=0). For no input pulses (A=B=0) there is no output pulse (C=0). This result describes the exclusive-OR (XOR) logical operation.

APPENDIX A $$E_{10} = E_{30}/\sqrt{2} + i\, E_{40}/\sqrt{2} \tag{1a}$$

$$E_{20} = i\, E_{30}/\sqrt{2} + E_{40}/\sqrt{2} \tag{1b}$$

$$E_3 = E_1/\sqrt{2} + i\, E_2/\sqrt{2} \tag{1c}$$

$$E_4 = i\, E_1/\sqrt{2} + E_2/\sqrt{2} \tag{1d}$$

$$E_{40} = E_3 \exp[i\{\beta L + \psi(t)\}] \tag{2a}$$

$$E_{30} = E_4 \exp[i\{\beta L + \psi'(t)\}], \tag{2b}$$

where $\beta$ is the propagation constant and $\psi$, $\psi'$ are the nonlinear phase shifts introduced by the nonlinear element 16.

$$E_{10} = i/2\{\exp[i\psi(t)] + \exp[i\psi'(t)]\}\exp(i\beta L)E_1 \tag{3a}$$

$$E_{20} = 1/2\{\exp[i\psi(t)] - \exp[i\psi'(t)]\}\exp(i\beta L)E_1 \tag{3b}$$

$$\psi(\tau_1) = \psi'(\tau_2) = \frac{2\pi}{\lambda} l \int_{-\infty}^{t} |E(t')|^2 \{n_T \exp[(t' - t)/t_T] + n_E \exp[(t' - t)/t_E]\} dt' \tag{4}$$

where $\tau_1 = t - xL/v$, $\tau_2 = t - (1-x)L/v$, xL and (1−x)L being the distance of portion 16 from the ports 10 and 12 respectively, and $v$ being the group velocity; $|\overline{E}(t)|^2$ is the total intensity of the optical signals at the nonlinear element 16, and $t_T$, $t_E$ are, respectively, the relaxation times associated with the thermal and electronic nonlinearity of the element 16, the coefficients for the thermal and electronic nonlinearity being $n_T$ and $n_E$ respectively.

$$\psi(\tau_1) = \psi'(\tau_2) = \Phi_T + K \int_{-\infty}^{t} |E(t')|^2 \exp[(t'-t)/t_E] dt', \quad (5)$$

where $$\Phi_T = \frac{2\pi}{\lambda} l\, n_T t_R \int_{-\infty}^{+\infty} |E(t)|^2 dt, \quad (5a)$$

$$K = \frac{2\pi}{\lambda} l\, n_E, \quad (5b)$$

and $\int dt$ denotes the integral when the device is operated for a single cycle, i.e., a single pair of counter-propagating pulses incident at the nonlinear element.

$$\psi(t) = \Phi_T + K \int_{-\infty}^{t} |E_3(t')|^2 dt' \quad (6a)$$

$$\psi'(t) = \Phi_T + \quad (6b)$$

$$K \left\{ \exp(-t_D/t_E) \int_{-\infty}^{+\infty} |E_3(t)|^2 dt + \int_{-\infty}^{t} |E_4(t')|^2 dt' \right\}$$

$$E_{20} = \tfrac{1}{2}[1 - \exp(i\theta)] \exp\left[ i\left( \Phi_T + \tfrac{1}{2} K \int_{-\infty}^{t} |E_1(t')|^2 dt' \right) \right] E_1 \quad (7)$$

where $$\theta = \tfrac{1}{2} K \exp(-t_D/t_E) \int_{-\infty}^{+\infty} |E_1(t)|^2 dt. \quad (7a)$$

$$\frac{|E_{20}|^2}{|E_1|^2} = \frac{1-\cos\theta}{2}. \quad (8)$$

$$\theta_{A,B} = \tfrac{1}{2} K \exp(-t_D/t_E) \int_{-\infty}^{+\infty} |E_{A,B}(t)|^2 dt = \pi, \quad (9)$$

where $\int_{-\infty}^{+\infty} |E_{A,B}(t)|^2 dt$ here denotes an integral over a single A or B pulse at the input port 6.

We claim:

1. An optical device comprising a coupling means having a first and a second pair of optical communication ports in which optical pulse signals received at a port of one pair are coupled substantially equally into each port of the other pair, and an optical waveguide optically coupling together the first pair of ports, the optical waveguide including a portion of a material located non-equidistantly between the first pair of ports and having a non-linear refractive index with a relaxation time such that the effect on the non-linear portion of the first counter propagating pulse to pass through the portion lasts long enough to alter the phase of the second counter propagating pulse relative to the first pulse.

2. An optical device as claimed in claim 1 in which the non-linear portion is located just sufficiently far from the midpoint of the waveguide to prevent the counter propagating pulses overlapping within the portion for a predetermined input pulse.

3. An optical device as in claim 1 or 2 in which the non-linear portion is of Cd $S_x Se_{1-x}$ doped glass.

4. An optical device as in claim 1 or 2 in which the waveguide is monomode optical fibre.

5. An optical device as claimed in claim 1 or 2 in which the waveguide is a planar waveguide.

6. An optical device comprising an optical waveguide loop coupled between a pair of optical coupler ports and including a section disposed non-equidistantly from the ports which section exhibits a non-linear optical parameter capable of altering the relative phase of counter propagating light pulses within the loop.

7. A method of achieving relative phase shifts between counter-propagating light pulses within an optical waveguide loop disposed between a pair of optical coupler ports, said method comprising the step of:
introducing a non-linear optical signal transfer parameter within the loop at a location non-equidistantly disposed from said ports.

* * * * *